United States Patent [19]
Davis et al.

[11] Patent Number: 5,899,692
[45] Date of Patent: May 4, 1999

[54] ILLUMINATED SYRINGE TIP AND HANDPIECE ASSEMBLY

[76] Inventors: Warren Davis, 942 Eldorado La., Las Vegas, Nev. 89123; David Wasserman, 2095 Mohigan Way, Las Vegas, Nev. 89109; Robert Dybus, 1437 Rawhide Rd., Boulder City, Nev. 89005

[21] Appl. No.: 08/932,070

[22] Filed: Sep. 17, 1997

Related U.S. Application Data

[63] Continuation of application No. 08/711,284, Sep. 9, 1996, abandoned, which is a continuation-in-part of application No. 08/438,275, May 10, 1995, abandoned, and a continuation-in-part of application No. 08/485,009, Jun. 7, 1995, abandoned.

[51] Int. Cl.$^6$ .................................................. A61C 17/00
[52] U.S. Cl. .............................. 433/80; 433/29; 433/84; 433/87
[58] Field of Search .................. 433/29, 80, 81, 433/82, 88, 89, 84, 87

[56] References Cited

U.S. PATENT DOCUMENTS

| | | | |
|---|---|---|---|
| 3,010,357 | 11/1961 | Hirschowitz | 88/1 |
| 4,080,737 | 3/1978 | Fleer | 32/22 |
| 4,507,085 | 3/1985 | Mosimann et al. | 433/126 |
| 4,619,612 | 10/1986 | Weber et al. | 433/80 |
| 4,629,425 | 12/1986 | Detsch | 433/31 |
| 4,648,838 | 3/1987 | Schlachter | 433/29 |
| 4,886,455 | 12/1989 | Lohn | 433/80 |
| 5,088,924 | 2/1992 | Woodward | 433/126 |

OTHER PUBLICATIONS

Fiberoptics Technology Incorporated Catalog, p. 25, (undated).

*Primary Examiner*—Nicholas D. Lucchesi
*Attorney, Agent, or Firm*—John Edward Roethel

[57] ABSTRACT

A dental syringe tip handpiece assembly includes a clear, plastic syringe tip mounted in an adaptor for connection to the handpiece. On the interior of the adaptor at a location adjacent the end of the syringe tip, a source of light, preferably a fiberoptic ringlight, is provided. Light from the light source will be transmitted down the length of the syringe tip and emitted from the end thereof. By positioning the end of the syringe tip in the patient's oral cavity, the dentist can provide illumination in the oral cavity so that various dental functions can be more easily and accurately performed. The source of light may also be a light bulb positioned at the rear of the adaptor. The adaptor is made from clear, or at least translucent, material so that light from the light bulb will be transmitted through the adaptor and then into the syringe tip. A special handpiece body formed of a handpiece inner unit and an outer cover is provided to receive the adaptor and syringe tip assembly. The air, water and fiberoptic lines are positioned inside the handpiece body. The handpiece body can be easily disassembled for cleaning. Alternatively one or more fiberoptic bundles are disposed through the handle of the syringe tip assembly with the ends of the fiberoptic bundle positioned adjacent the syringe tip so that light from the fiberoptic bundle can be transmitted through the syringe tip.

4 Claims, 11 Drawing Sheets

ILLUMINATED SYRINGE TIP AND HANDPIECE ASSEMBLY

This is a continuation of application Ser. No. 08/711,284, filed Sep. 9, 1996, now abandoned.

CROSS-REFERENCE TO RELATED APPLICATIONS

This application is a continuation-in-part of application Ser. No. 08/438,275, filed May 10, 1995, entitled "Illuminated Syringe Tip and Handpiece Assembly", now abandoned, and a continuation-in-part of application Ser. No. 08/485,009, filed June 7, 1995, entitled "Illuminated Syringe Tip and Handpiece Assembly", now abandoned.

BACKGROUND OF THE INVENTION

This invention relates to an illuminated syringe tip and handpiece assembly, and more particularly to an illuminated syringe tip and handpiece assembly in which a disposable syringe tip is used to transmit light from a light source on the interior of the adaptor to the oral cavity of the patient to provide illumination for the dentist.

U.S. Pat. No. 5,049,071 (Davis et al.) discloses a disposable dental syringe tip made of plastic material. This patent also discloses various adaptors that can be used to attach the disposable syringe tip to the handpiece of a three way dental syringe assembly. The disclosure of this U.S. Pat. No. 5,049,071 is incorporated herein by this reference. Additionally, U.S. Pat. No. 5,192,206 (Davis et al.) contains additional disclosure relating to adaptors for use in three way dental syringe assemblies and the disclosure of this U.S. Pat. No. 5,192,206 is also incorporated herein by this reference.

The use of disposable plastic syringe tips has become quite widespread in light of the serious concern about the rising incidence of communicable diseases such as hepatitis and acquired immune deficiency syndrome. Dentists are taking extreme care to prevent the transmission of germs (viral or bacteria) from one patient to the next. The plastic syringe tip receives air and water under pressure. By operation of the air button and the water button on the handpiece, the dentist can direct water, air or a combined air/water spray into the patient's mouth for whatever dental procedures are required.

It is desirable to also supply light into the oral cavity to assist the dentist in performing necessary dental procedures. Most dental operators have an overhead lighting system with reflective surfaces that help concentrate the light on the patient's mouth. However, the dentist will often stand in the path of the light which minimizes the effectiveness of the overhead light.

Various dental tools have been provided with a light source to assist the dentist during various dental activities. For example, a typical dental drill will include a fiberoptic bundle that transmits light from a light source to the end of the dental drill which allows the dentist to provide light directly to the area in which the drilling is occurring. Representative of this technology are the disclosures shown in U.S. Pat. No. 4,507,085 (Mosimann) and U.S. Pat. No. 5,088,924 (Woodward).

Dental syringe tip handpieces have also been provided with a light source to illuminate the area into which the air and/or water are to be sprayed. Representative of these devices is the disclosure of U.S. Pat. No. 4,619,612 (Weber) which shows a fiberoptic bundle disposed down the center of a metal syringe tip assembly. A light bulb acts as the light source and is disposed in the interior of the handpiece. The syringe tip used in the disclosure of the Weber patent is a metal, non-disposable syringe tip which must be autoclaved prior to use on the next patient.

Prior to the present invention, however, there have not been any disposable syringe tips provided with a light source to transmit light to the oral cavity. Dentists using disposable syringe tips would have had to rely on the ambient overhead lighting systems, used in the dental operators in order to see in the oral cavity of the patient during use of the air/water dental syringe tip handpiece.

It is an object of the present invention to provide a useful source of light that can be transmitted into the oral cavity of the patient whenever the dentist is using an air/water dental syringe tip handpiece.

It is a feature of the present invention to provide a light source at the end of the syringe tip on the interior of the adaptor that holds the syringe tip in the dental syringe tip handpiece. Light from the light source is directed into one end of the syringe tip and carried along the length thereof. At the opposite end of the syringe tip, the light radiates from the syringe tip and can be used to illuminate the oral cavity of the patient.

It is an advantage of the present invention that a dentist will be able to illuminate the oral cavity using the same instrument that he is using to supply air, water or combined air and water to the oral cavity of the patient. Any dental procedures that require use of the air/water dental syringe tip handpiece will be more easily, safely and effectively carried out because the dentist will be able to see exactly where in the oral cavity he is working.

Other objects, features and advantages of the present invention will become apparent from a consideration of the following detailed description.

SUMMARY OF THE INVENTION

A dental syringe tip handpiece assembly includes a clear, plastic syringe tip mounted in an adaptor for connection to the handpiece. On the interior of the adaptor at a location adjacent the end of the syringe tip, a source of light, preferably a fiberoptic ringlight, is provided. Light from the light source will be transmitted down the length of the syringe tip and emitted from the end thereof. By positioning the end of the syringe tip in the patient's oral cavity, the dentist can provide illumination in the oral cavity so that various dental functions can be more easily and accurately performed.

A special handpiece body formed of a handpiece inner unit and an outer cover is provided to receive the adaptor and syringe tip assembly. The air, water and fiberoptic lines are positioned inside the handpiece body. The handpiece body can be easily disassembled for cleaning.

The source of light may also be a light bulb positioned at the rear of the adaptor. The adaptor is made from clear, or at least translucent, material so that light from the light bulb will be transmitted through the adaptor and then into the syringe tip.

In yet another embodiment of the present invention, the source of the light may be one or more fiberoptic bundles disposed through a valve head and a manifold assembly. The ends of the fiberoptic bundles are positioned adjacent the end of a syringe tip so that the light emitting from the ends of the fiberoptic bundles is transmitted into the syringe tip which then carries the light along the length thereof and the light is emitted from the end of the syringe tip and can be used to illuminate the oral cavity of a patient.

DETAILED DESCRIPTION OF THE PREFERRED EMBODIMENTS

Figure 1:
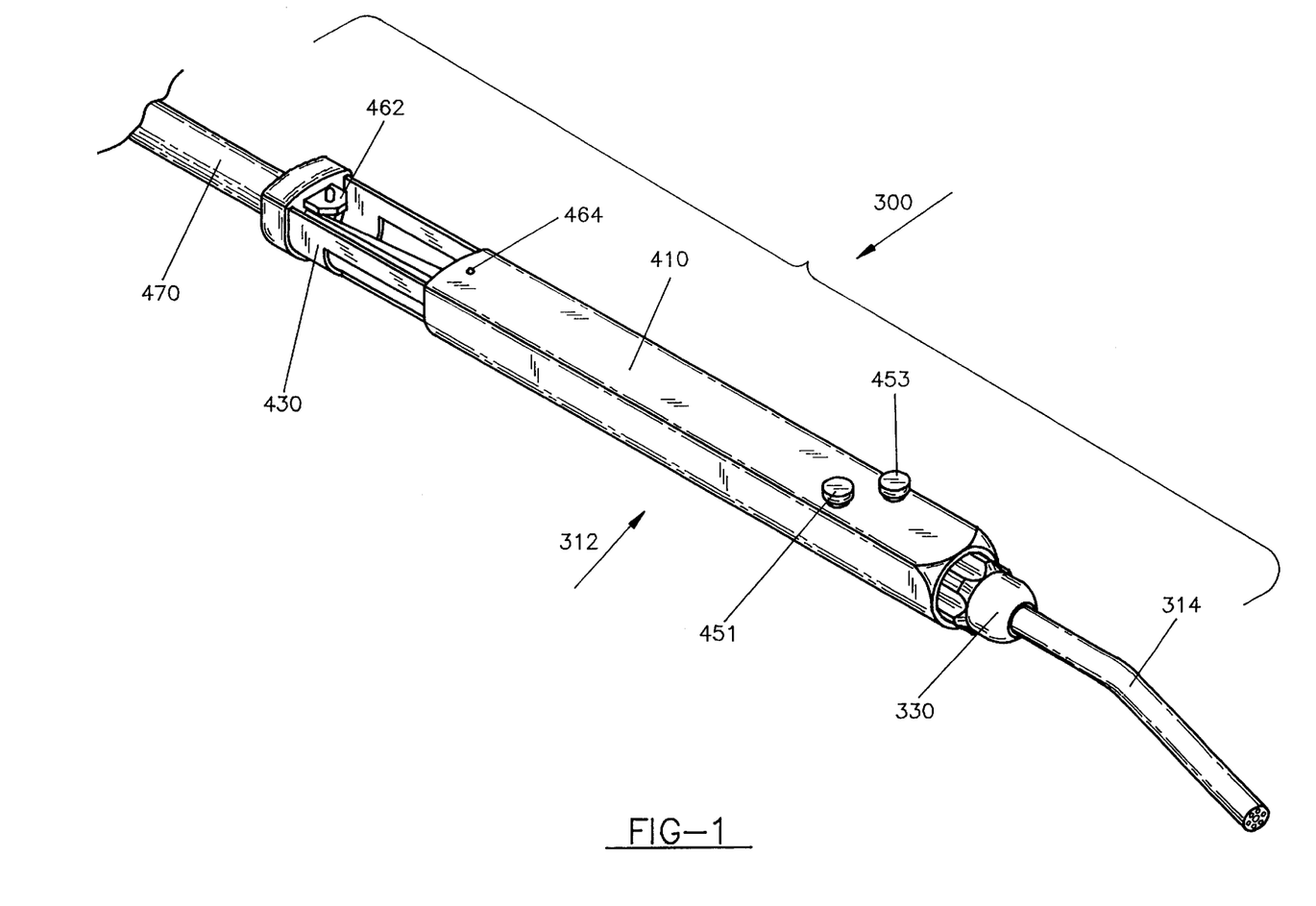
FIG. 1 shows a partially-exploded isometric view of the illuminated syringe tip assembly and a handpiece body of the present invention.

The illuminated dental syringe tip handpiece assembly of the present invention is shown generally at 300 in FIG. 1. A handpiece body 312 comprises an outer cover 410 that slidably mounts over an inner unit 430. The inner unit 430 is a generally U-shaped channel that has a hollow interior to accommodate the water line, the air line and a fiberoptic line. Each of these supply lines are connected to the handpiece body 312 by means of an outer tubing 470 which extends to the sources (not shown) of the water supply, the air supply and the light source for the fiberoptic line.

At one end of the handpiece body 312, there is provided an adaptor 320 that mounts the syringe tip 314 into the handpiece body 312. A locking cap assembly 330 holds the syringe tip 314 securely in place.

Figure 2:
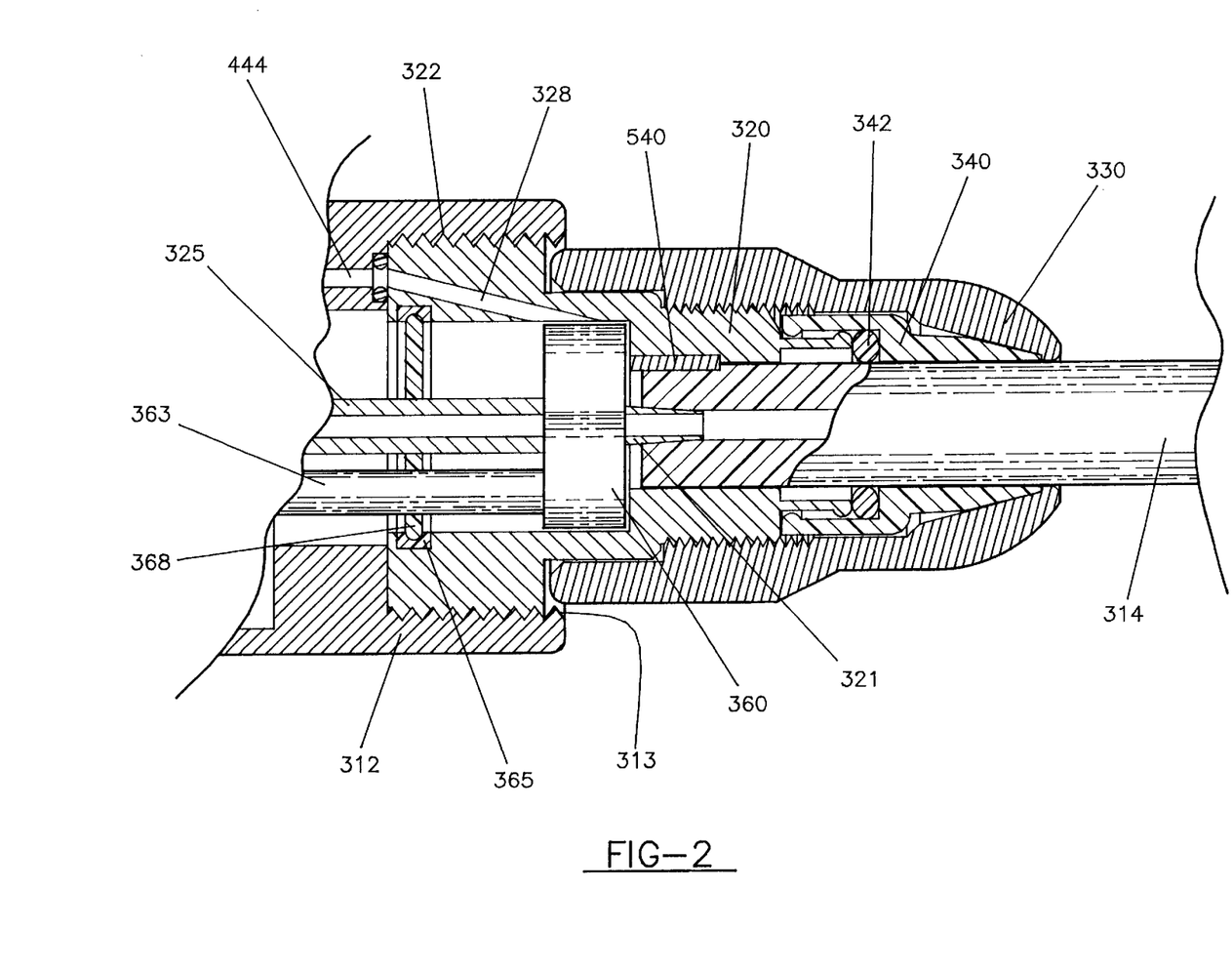
FIG. 2 shows a cross sectional view at the location in the assembly at which the adaptor, syringe tip and locking cap are joined to the handpiece body, with all parts in the closed position.
Figure 3:
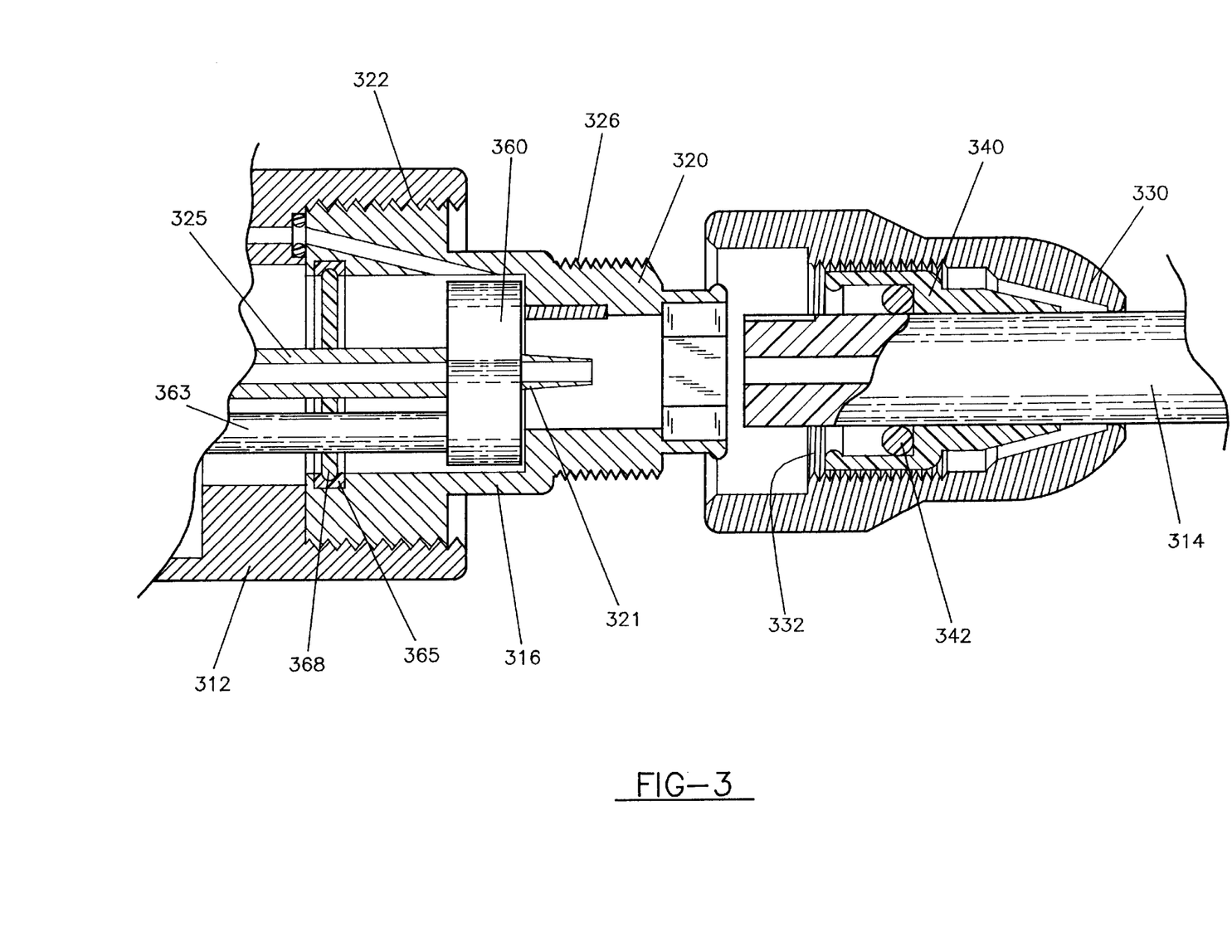
FIG. 3 shows a cross sectional view at the location in the assembly at which the adaptor, syringe tip and locking cap are joined to the handpiece body, with all parts in the open position.
Figure 5:
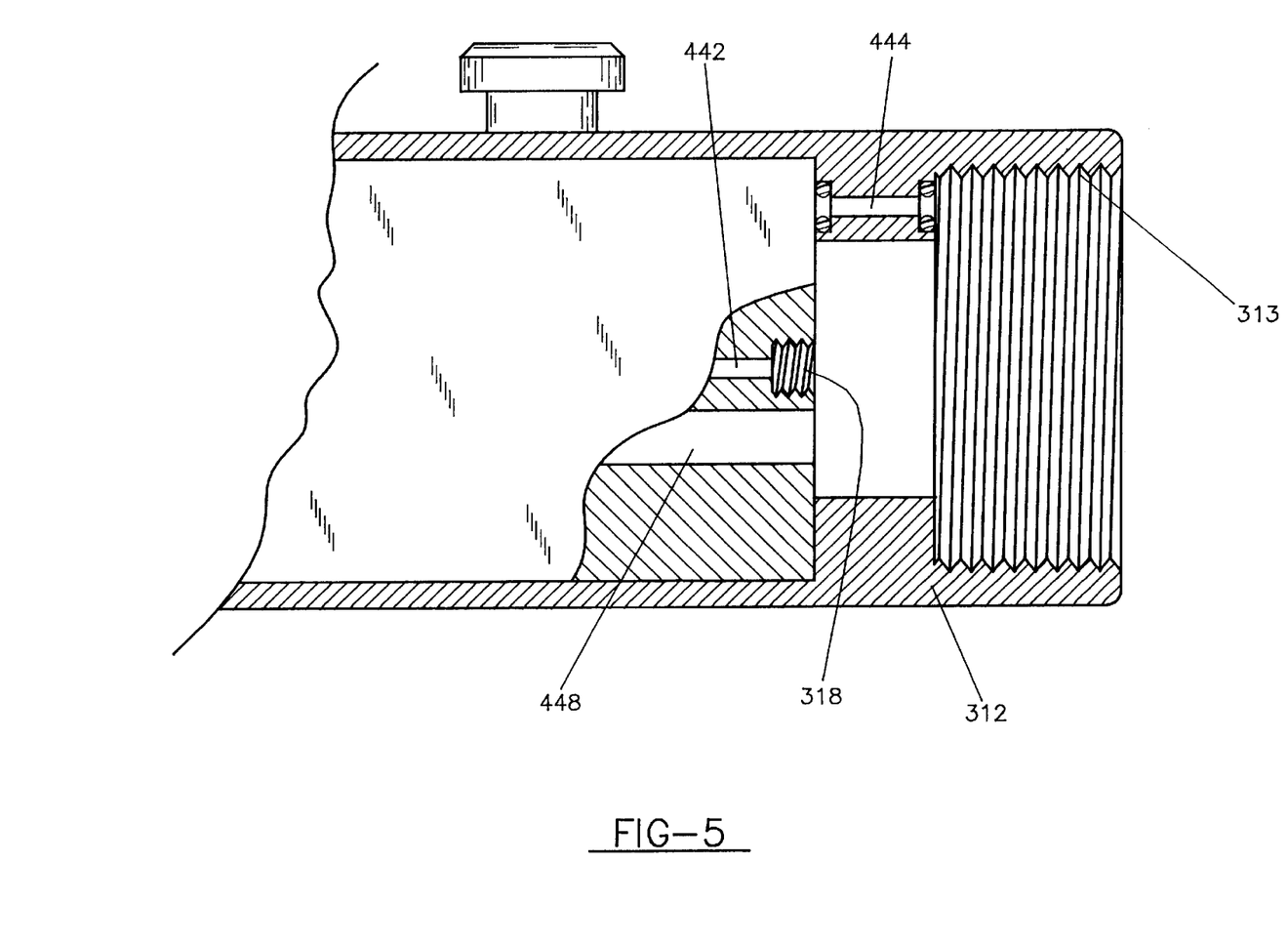
FIG. 5 shows a cross section of one end of the hand-piece body shown in FIG. 4.

As shown in FIGS. 2, 3 and 5, the handpiece body 312 has at one end a threaded opening 313 into which the adaptor 320 can be screwed using the first adaptor threads 322. The middle of the adaptor 320 is provided with a central hexagonal opening 316 into which a wrench can be positioned to tighten the adaptor 320 into the threaded opening 313 of the handpiece body 312.

In the embodiment shown in this application, the handpiece body can be a standard configuration known as the "Continental Design," although the components of the present invention can be modified to fit any handpiece body configuration. Further details of the adaptor 320 are set out in U.S. Pat. No. 5,049,071, which is incorporated herein by this reference.

A locking assembly securely holds the syringe tip 314 into the handpiece body 312 to prevent inadvertent loosening of the syringe tip 314 so that the air and water supply is at all times fed through the syringe tip 314 and to prevent the syringe tip 314 from separating from the adaptor 320. The locking assembly comprises generally the adaptor 320, a collet gripping member 340 that fits over the exterior end of the adaptor 320, an O-ring 342 and a locking cap 330 that screws onto the adaptor 320 and surrounds the collet gripping member 340. The interior of the locking 330 contains a set of screw threads 332 that cooperate with the second adaptor threads 326 on the adaptor 320 to secure the locking cap 330 to the adaptor 320. Further details of the locking assembly are shown in U.S. Pat. No. 5,306,146 and U.S. Pat. No. 5,489,205, both of which are incorporated herein by this reference. The release of the locking cap 330 from the adaptor 320 takes pressure off the collet gripping member 340 which allows removal of a used syringe tip and replacement with a new syringe tip.

The syringe tip 314 is an elongated cylindrical member preferably made of a plastic material. The syringe tip 314 is press fit onto the tapered spindle 321 of the adaptor 320. Further details of the syringe tip are set out in U.S. Pat. No. 5,049,071. The syringe tip 314 must be made of material that will transmit light from one end of the syringe tip to the other end. In the preferred embodiment of the present invention, the syringe tip 314 is made of polypropanate, although other light transmitting, plastic materials can be used such as acrylic plastics.

Also, the syringe tip 314 preferably should be clear or transparent so that an inspection of the syringe tip would reveal if it had previously been used. Once a syringe tip has been used on a patient, the end of the syringe tip will retain small amounts of saliva, blood or other materials from the patient's mouth.

The syringe tip 314 is designed to be disposable after a single use. The tip material is fabricated in a single-step extrusion process, and is made preferably from any rigid transparent plastic that can transmit light. A rigid plastic is preferred to fulfill the need to use the tip for continued retraction of the cheek and tongue by the dental operator.

The syringe tip 314 is press fit onto the tapered spindle 321 at the end of the spindle extension 325. The tapered spindle 321 is integrally connected to an spindle extension 325 that extends through the rear end of the adaptor and into the handpiece body 312. The rear end of the spindle extension 325 is threaded and received by the threaded opening 316 on the interior of the handpiece body 312. The remote end of the spindle extension 325 is connected to the water supply line 444 which allows water to be feed to the syringe tip 314 in a conventional manner.

Similarly, the air supply is sent to the adaptor 320 through an air supply line 442 in the handpiece body 312 that aligns with the air channel 328 in the adaptor 320.

As shown in FIGS. 2 and 3, a light source in the form of a fiberoptic ringlight 360 is disposed directly adjacent to the end of the syringe tip 314 on the interior of the adaptor 320 so that light is directed down the length of the syringe tip. In the preferred embodiment of the present invention, a fiberoptic ring light made by Fiberoptics Technology Incorpo rated, 14 Fiber Road, Pomfret, Conn. 06258 can be used, although any suitable fiberoptic ring arrangement would be acceptable. The fiberoptic ringlight 360 is connected to a fiberoptic bundle 363 which extends through a passageway 448 in the handpiece body 312 for connection to a remote light source (not shown).

On the interior of the adaptor 320, there is provided an annular grommet 365 which receives a snap in flexible ring 368. This flexible ring 368 surrounds the spindle extension 325 and the fiberoptic bundle 363 and holds them in place on the interior of the adaptor 320.

As shown in FIG. 2, with the locking cap 330 pushed onto the adaptor 320 in the closed position, the fiberoptic ringlight 360 sits adjacent to the end of the syringe tip 314 in the interior of the adaptor 320. When the power supply is activated by the dentist, the light bulb 360 will illuminate and the light therefrom will be passed along the length of the syringe tip 314 to its remote end where it is emitted to illuminate the oral cavity of the patient.

Figure 4:
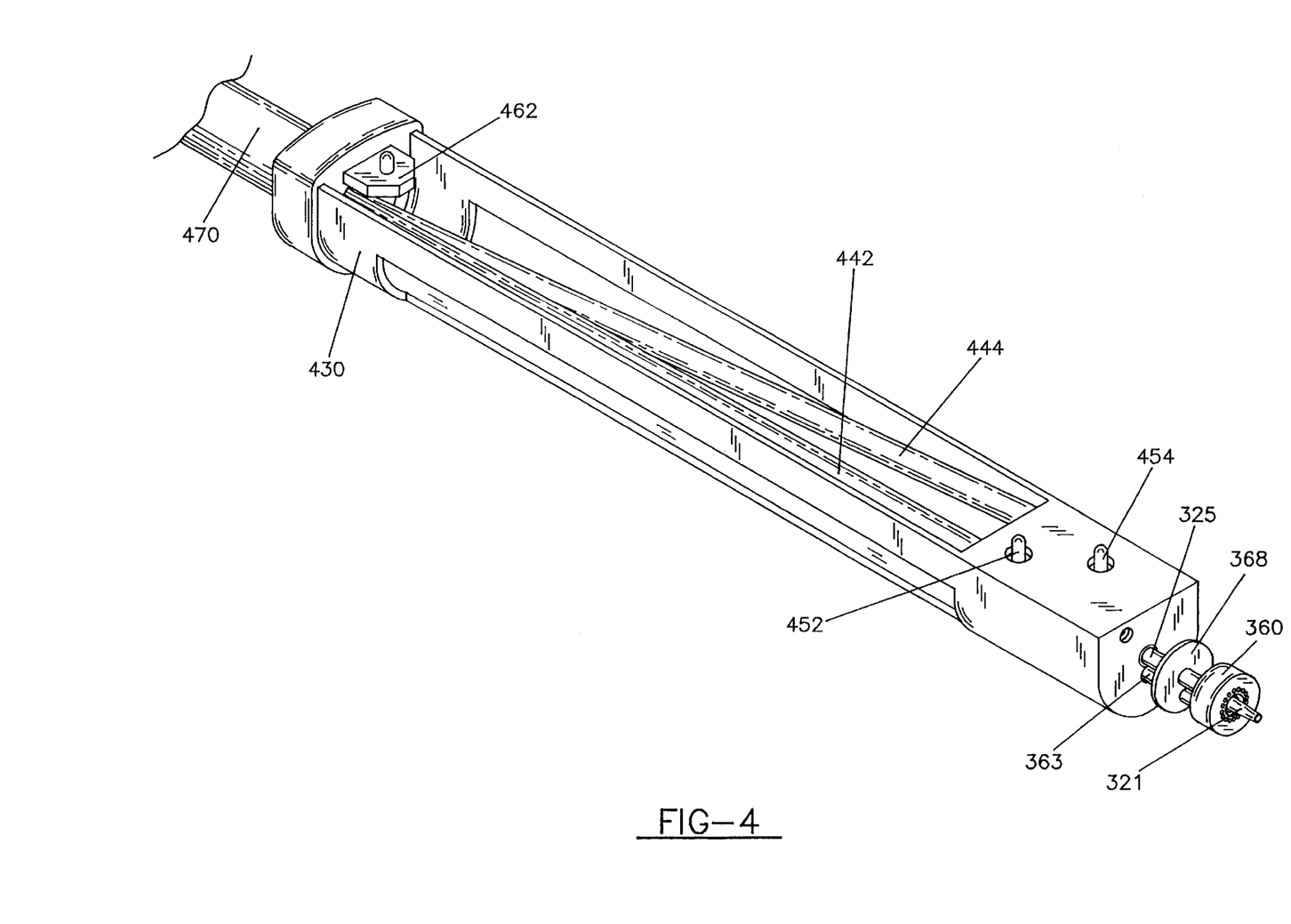
FIG. 4 shows an isometric view of the handpiece body of the present invention with the outer cover removed.

FIG. 4 shows the interior details of the inner unit 430 of the handpiece body 312. On the interior of the inner unit 430 inside the U-shaped channel, there is provided the water supply line 444 and the air supply line 442 which supply the air and water from the source to the adaptor. The water valve 454 is positioned in the water supply line 444 and is activated by the dentist by depressing the water button 453 carried by the outer cover 410. Similarly, air valve 452 is positioned in the air supply line 442 and is activated by the dentist by depressing the air button 451 carried by the outer cover 410.

The inner unit 430 is also provided with a conventional pin fastener 462 which cooperates with an aperture 464 in the outer cover 410. The outer cover 410 slides over the length of the inner unit 430 and the pin fastener 462 engages into the aperture 464 to hold the outer cover 410 in place when the assembly is being used. When it is desired to clean the assembly, the pin fastener 462 is depressed which allows the outer cover 410 to slide off of the inner unit 430. The adaptor 320 unscrews from the handpiece body 312 and the outer cover 410, the adaptor 320, the locking cap 330 and the collet gripping member 340 can then all be cleaned and autoclaved as needed.

Figure 6:
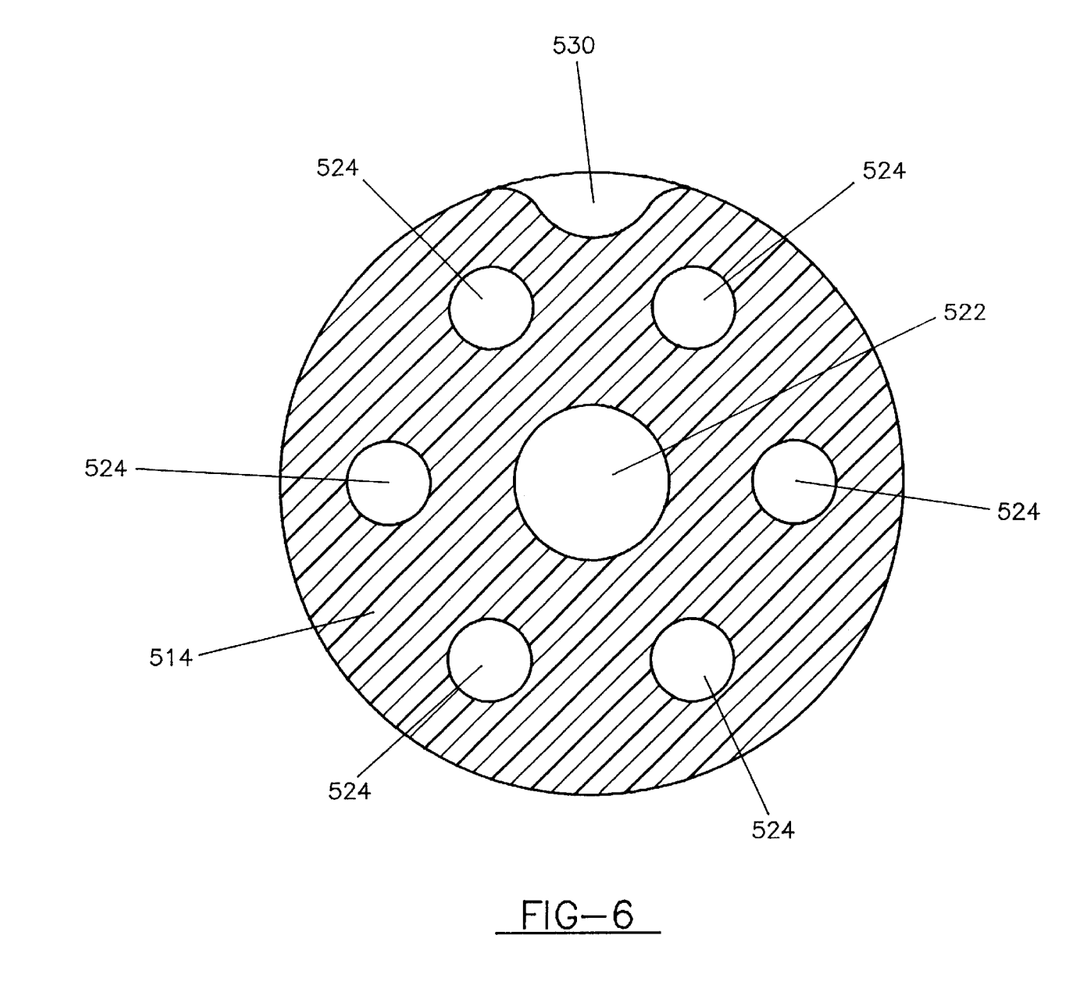
FIG. 6 shows a cross sectional end view of a syringe tip for use with the present invention.

FIG. 6 shows a modification to a syringe tip 514 which ensures that the syringe tip is accurately positioned in the adaptor 320. The syringe tip 514 has a central water passageway 522 and a plurality of air passageways 524 positioned around the water passageway 522. One end of the syringe tip 514 is provided with a keyed channel 530 which aligns with a complementary adaptor insert 540 (see FIG. 2) on the interior of the adaptor 320. Thus, for the syringe tip 514 to properly seat within the adaptor 320, the keyed channel 530 on the syringe tip 514 must be aligned with the adaptor insert 540. If the alignment is not correct, the adaptor 514 will not properly press fit onto the spindle 321 and water and air leakage problems will occur.

Other variations of the present invention may be made. Instead of the fiberoptic ringlight 360, other suitable light sources can be used. For example, any suitably shaped light bulb can be positioned on the interior of the adaptor so that light can then be transmitted down the syringe tip and into the oral cavity of the patient.

Figure 7:
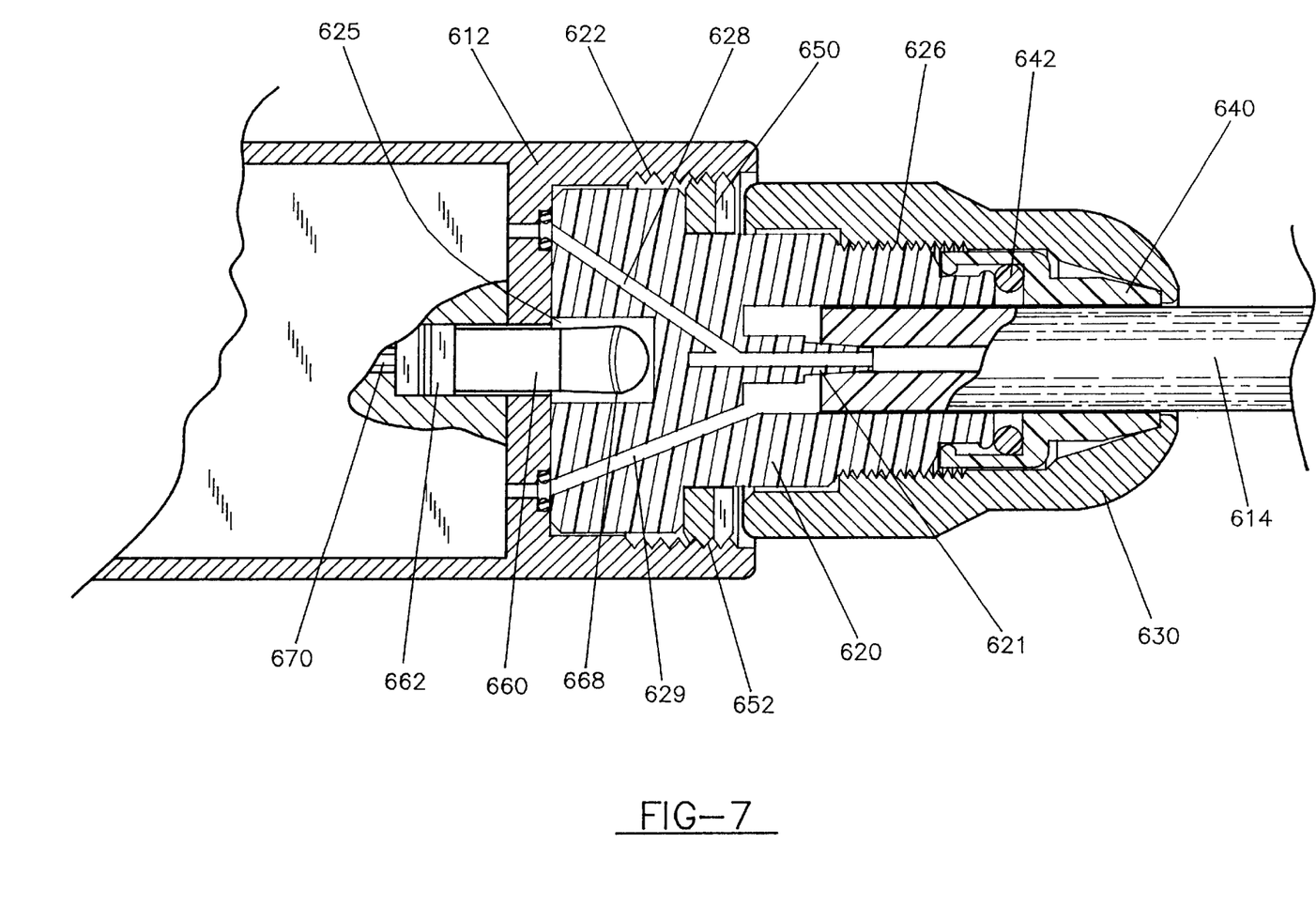
FIG. 7 shows a cross sectional view of a modified embodiment of the present invention at the location in the assembly at which a light bulb is positioned at the rear of the adaptor.

As shown in FIG. 7, the handpiece body 612 has an adaptor 620 that mounts the syringe tip 614 into the handpiece body 612. In this embodiment, the adaptor 620 is made of a relatively hard plastic such as polycarbonate or hard acrylics. The adaptor 620 must also transmit light from a light source 660 to the syringe tip 614, so the material chosen for the adaptor 630 must a light transmitting material. It is preferred that this material be a clear, transparent plastic, but a translucent material may also be used.

The adaptor 620 rests in one end of the handpiece body 612 and a locking ring 650 having an external locking ring thread 652 cooperates with a set of internal threads 622 holds the adaptor 620 in place. The locking ring 650 can have a recessed groove (not shown) on it surface to receive a screw driver for turning the locking ring 650 into the internal threads 622.

The adaptor 630 includes a tapered spindle 621 upon which the syringe tip 614 is mounted. A water channel 628 and an air channel 629 are provided in the adaptor 620 to transmit water and air, respectively, from the handpiece 612 to the syringe tip 614. A locking assembly securely holds the syringe tip 614 into the handpiece body 612 to prevent inadvertent loosening of the syringe tip 614 so that the air and water supply is at all times fed through the syringe tip 614 and to prevent the syringe tip 614 from separating from the adaptor 620. The locking assembly comprises generally the adaptor 620, a collet gripping member 640 that fits over the exterior end of the adaptor 620, an O-ring 642 and a locking cap 630 that screws onto the adaptor 620 and surrounds the collet gripping member 640. The interior of the locking 630 contains a set of screw threads that cooperate with the second adaptor threads 626 on the adaptor 620 to secure the locking cap 630 to the adaptor 620.

The adaptor 620 contains a bulb recess 625 that receives the light bulb 660. The light bulb 660 is mounted on a light bulb base 662 positioned in the handpiece body 612. The light bulb base 662 is connected to a remote power supply (not shown) by connecting wire 670.

When the light bulb 660 is activated by the power supply, a lens 668 concentrates the light into the adaptor 620 whence the light is transmitted through the adaptor 620 and into the syringe tip 614 for transmission to the mouth of the patient.

It is desirable to minimize heat being emitted from the light source, so fiberoptic or fluorescent light structures are preferred since the heat emissions of these light sources is minimal. It is also contemplated that a light source positioned adjacent a reflective surface can be used to focus the light into the end of the syringe tip. This would increase the light intensity without increasing the size of the light source and would increase the light intensity available for transmission down the length of the syringe tip.

As shown in FIGS. 8–12, another embodiment of the present invention utilizes one or more fiberoptic bundles to deliver light from a light source through the handle of the syringe tip assembly into the syringe tip where the light is transmitted the length of the syringe tip and used to illuminate the oral cavity of the patient.

Figure 8:
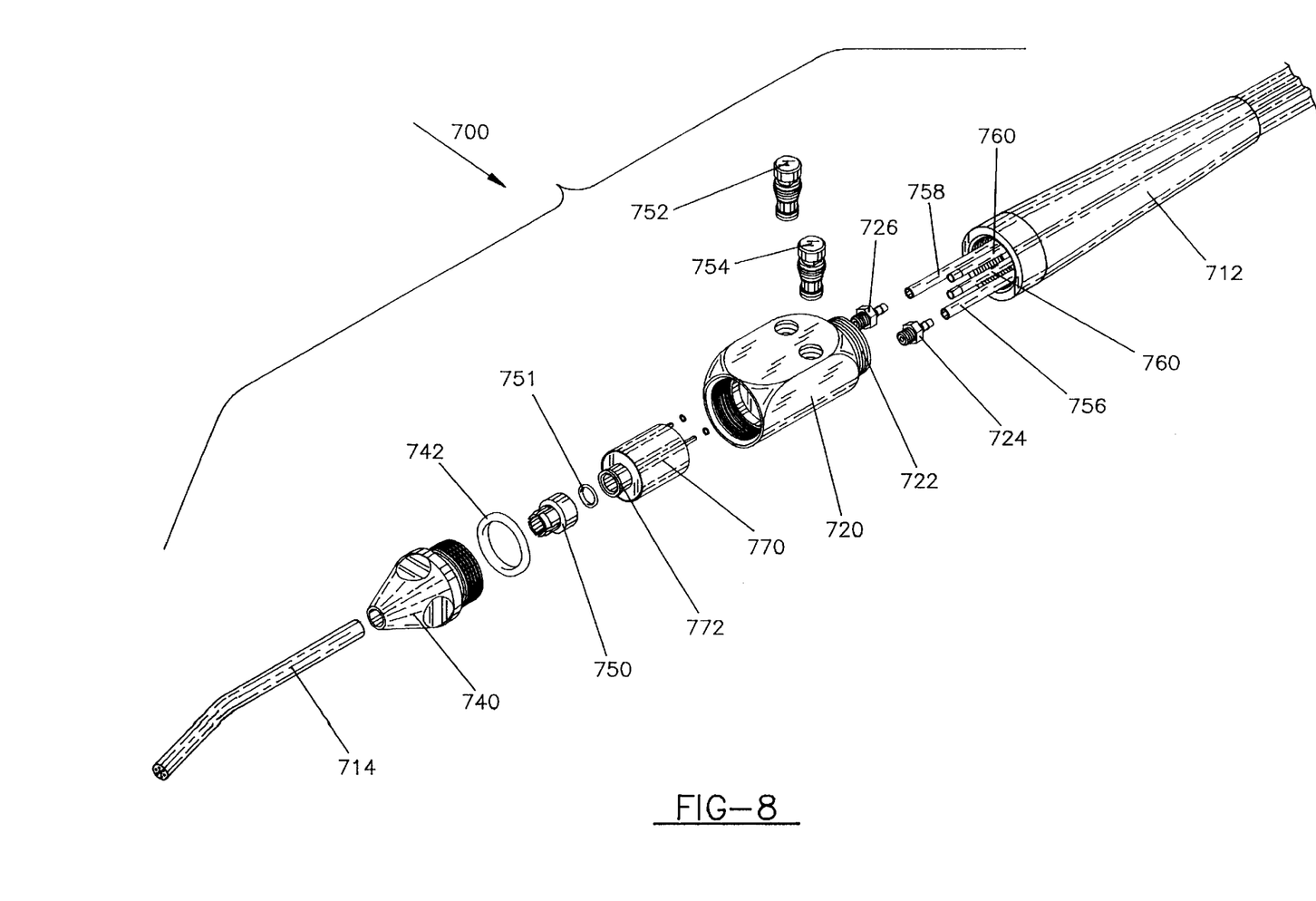
FIG. 8 shows a partially-exploded isometric view of another alternative embodiment of an illuminated dental syringe tip assembly of the present invention.
Figure 9:
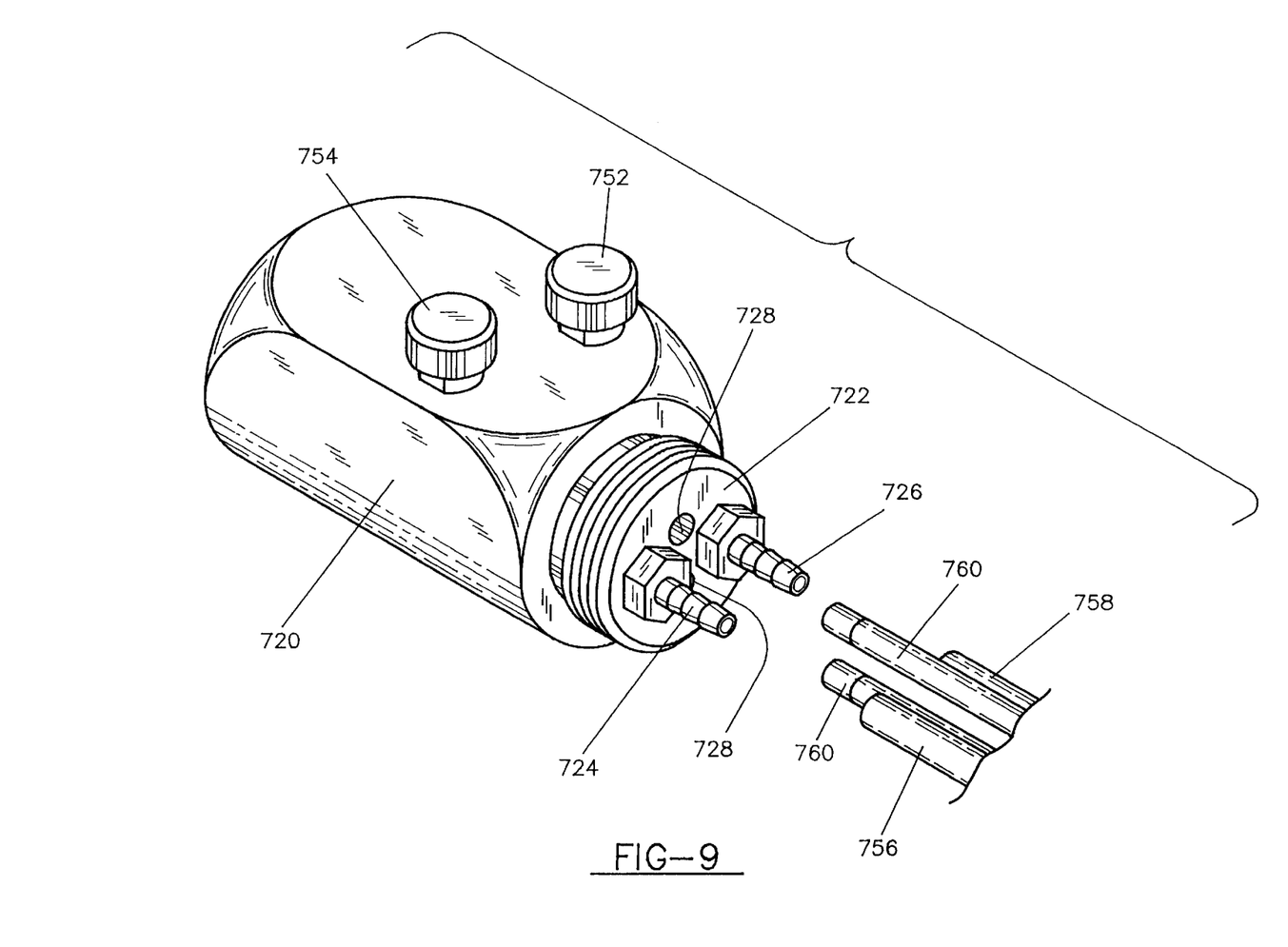
FIG. 9 shows a partially exploded isometric view of the head and fiberoptic bundles used in this alternative embodiment of the present invention.

The dental syringe assembly of this embodiment is shown generally at 700. The handle 712 contains the connecting lines for the fiberoptic bundles 760 and for the sources of air and water which are water tubing 756 and air tubing 758. The handle 712 threads (or otherwise suitably connects) to a head 720 having a threaded extension 722. The head 720 also contains the air valve 752 and the water valve 754 for activation of the air and water, respectively, in a conventional manner. As shown in FIG. 9, the threaded extension 722 includes one or more fiberoptic bundle apertures 728 for receiving one or more of the fiberoptic bundles 760 as well as a water barb fitting 724 for connecting the water tubing 756 and an air barb fitting 726 for connecting the air tubing 758.

The head 720 also threadably connects to a thumb nut 740, which in operable relationship with a locking collar 750, securely holds the syringe tip 714 in place in the dental syringe assembly 700. The structure of the thumb nut 740 and locking collar 750 are shown in U.S. Pat. No. 5,306,146 and U.S. Pat. No. 5,489,205, the disclosures of which are incorporated herein by reference.

Figure 11:
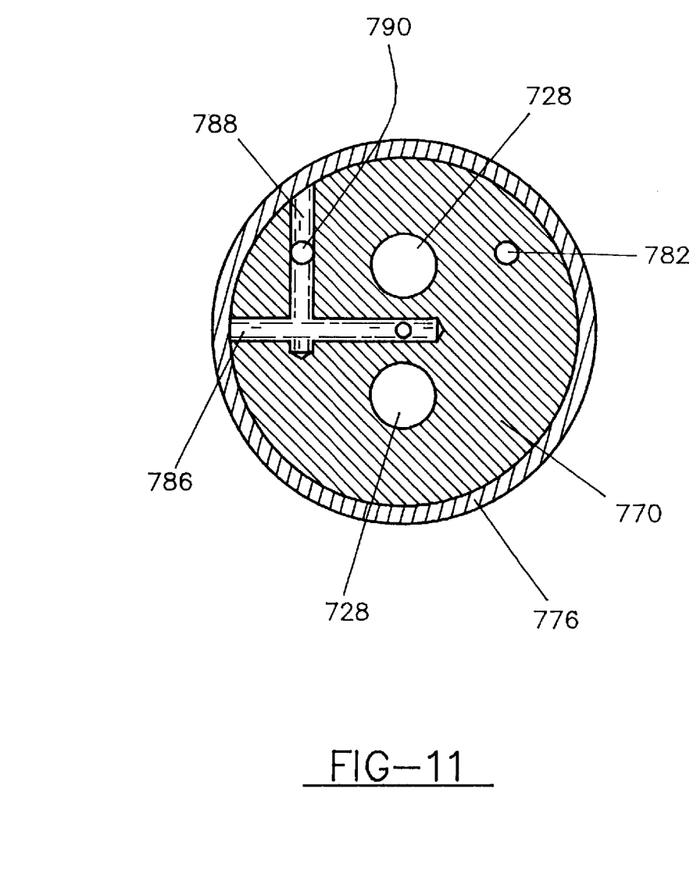
FIG. 11 shows a lateral cross section view of the manifold body used in this alternative embodiment and showing the location of the water veins.
Figure 12:
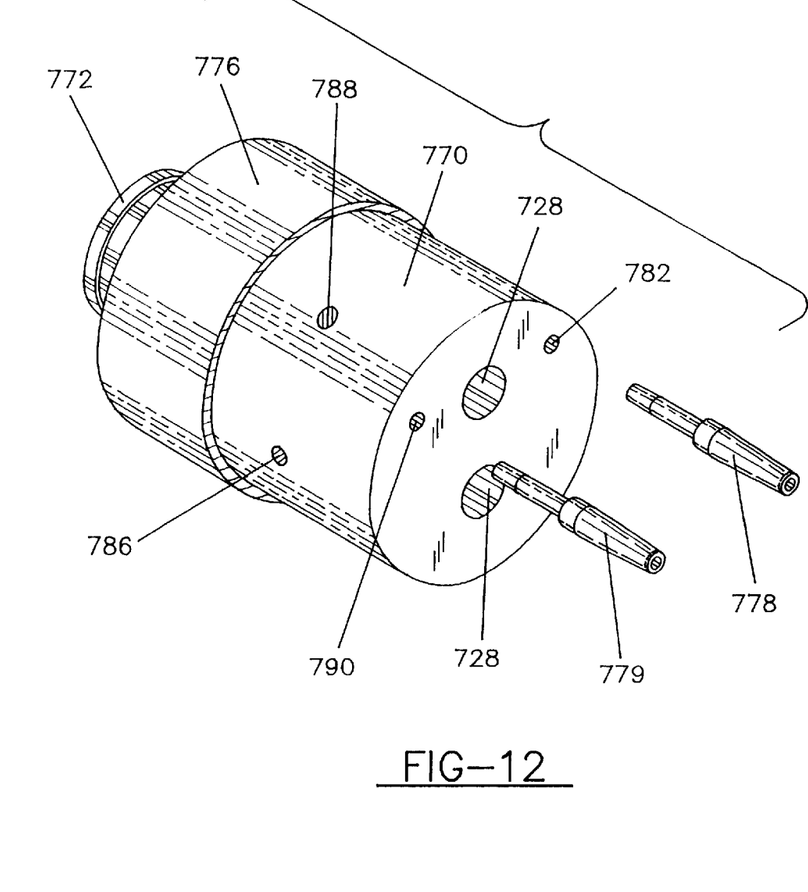
FIG. 12 shows a partially exploded isometric view of the manifold body, with the manifold sleeve partially cutaway, used in this alternative embodiment.

Positioned on the interior of the head 720 is a manifold body 770. The manifold body 770 is a generally cylindrical body which includes a tapered spindle 780 (see FIG. 10) upon which is mounted the syringe tip 714 in the manner shown in U.S. Pat. No. 5,236,356. A manifold top 772 is positioned next to the manifold body 770 and held in place thereat by a manifold sleeve 776. The manifold body 770 contains the fiberoptic bundle apertures 728 for receiving the fiberoptic bundles 760. The air supply for the dental syringe assembly 700 is connected to the air insert stem 778 which in turn is mounted in the air vein 782 which is a longitudinal passageway through the manifold body 770. The water supply for the dental syringe assembly 700 is connected to the water insert stem 779 which in turn is mounted in the offset longitudinal water vein 790 in the manifold body 770. The offset longitudinal water vein 790 intersects with a perpendicular water vein 788 in the manifold body 770, which also intersects with an axial water vein 786 in the manifold body 770 which finally intersects with a central longitudinal water vein 784 in the manifold body 770 to deliver water into the spindle 780 and from there into the syringe tip 714.

Figure 10:
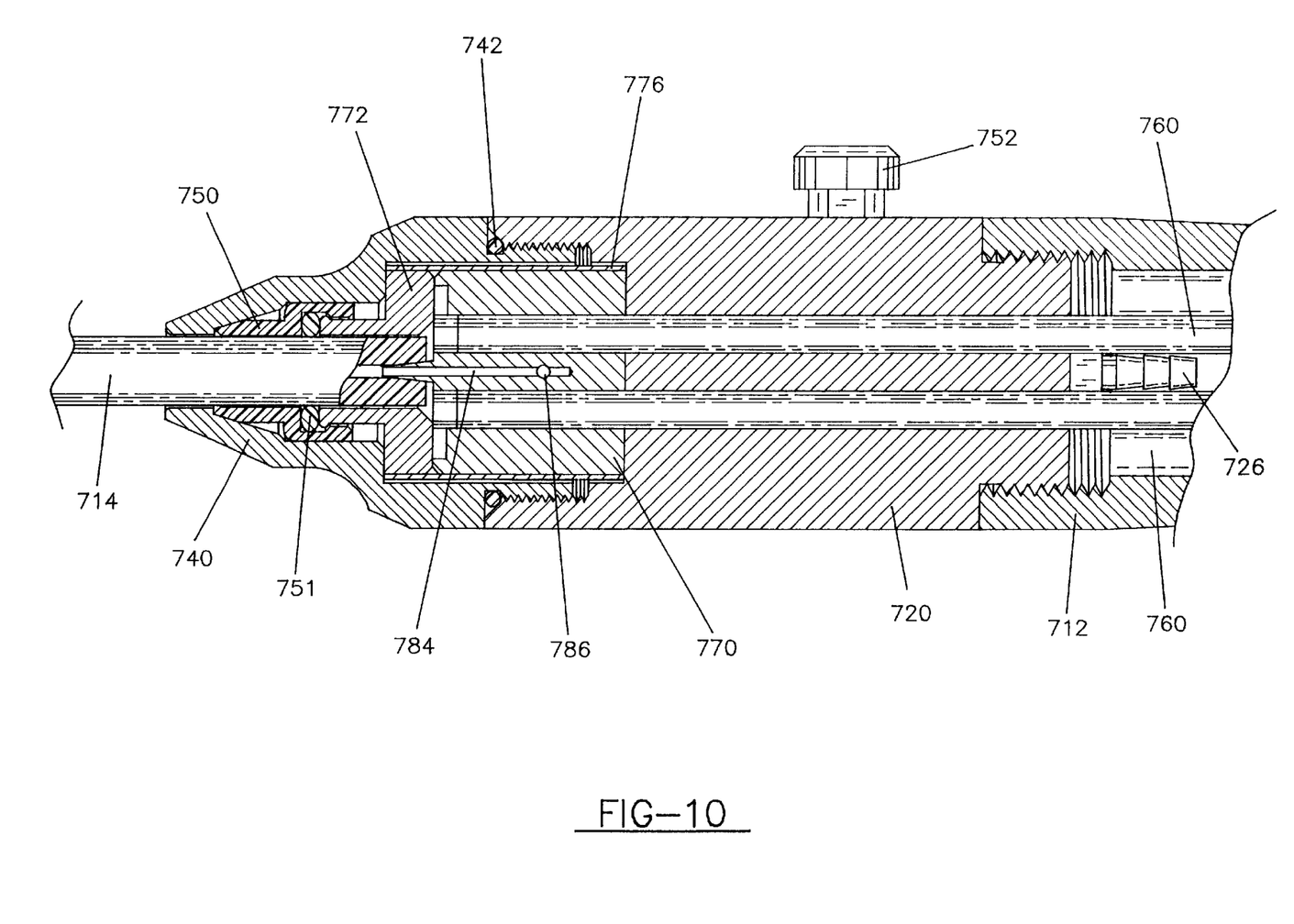
FIG. 10 shows a longitudinal cross sectional view in the closed position of this alternative embodiment of the present invention.

FIG. 10 shows in longitudinal cross section the dental syringe assembly 700 in assembled relationship. The head 720 is threaded into the handle 712 and the combined manifold body 770, manifold top 772 and manifold sleeve 776 are received in a recess in the head 720. The thumb nut 740 when threaded into the head 720 holds the manifold body 770, manifold top 772 and manifold sleeve 776 in place with an O-ring 742 provided to seal this threaded connection. The syringe tip 714 is pushed into the thumb nut 740 and one end thereof presses onto the spindle 780. The syringe tip 714 is securely held on the spindle 780 by the locking collar 750 and the O-ring 751 when the thumb nut 740 is threaded into the head 720.

The end of the syringe tip 714 is closely positioned to the ends of the fiberoptic bundles 760 so that when the light source (not shown) is activated, the light carried by the fiberoptic bundles 760 is transmitted into the end of the syringe tip 714 and is carried along the length of the syringe tip 714 where it can be emitted into the oral cavity of patient to provide needed illumination. Any suitable means can be used to activate the light source.

At the same time the light is being activated, the dentist can press the air valve 752 which causes air from the air tubing 758 to pass through the air vein 782 and into the air passageways in the syringe tip 714. Similarly, activation of the water valve 754 causes water from the water tubing 756 to pass into the offset longitudinal water vein 790, from there into the perpendicular water vein 788, from there into the axial water vein 786 and from there into the central longitudinal water vein 784 which connects to the central passageway in the spindle 780 which feeds water to the central water passageway of the syringe tip 714.

While the invention has been illustrated with respect to several specific embodiments thereof, these embodiments should be considered as illustrative rather than limiting Various modifications and additions may be made and will be apparent to those skilled in the art. Accordingly, the invention should not be limited by the foregoing description, but rather should be defined only by the following claims.

What is claimed is:

1. A dental syringe tip handpiece assembly for providing light for emission from a clear, light transmitting syringe tip comprising:

a) a generally hollow handle containing a light source, a water source and an air source;

b) a valve head attached to the handle, the valve head including a water valve and an air valve;

c) a manifold assembly positioned inside the valve head, the manifold assembly including a spindle adapted to receive a syringe tip to be mounted thereon;

d) the manifold assembly further including a water vein for transporting water from the water source to the spindle;

e) the manifold assembly further including an air vein for transporting air from the air source and adapted to provide air to a syringe tip; and f) the manifold assembly further including means for transmitting light from the light source to a location adjacent the spindle whereby when the light source is illuminated, light will be directed from the light source into a proximate end of a syringe tip to be mounted on the spindle so that light may be transmitted along the length of the syringe tip and emit from a remote end thereof whereby a dentist may illuminate a work area using the light emitting from the syringe tip.

2. The assembly of claim 1 further including a light transmitting syringe tip mounted on the spindle.

3. A dental syringe tip handpiece assembly for providing light for emission from a remote end of a clear, light transmitting syringe tip comprising:

a) a generally hollow handle containing at least one fiberoptic bundle, a water source tubing and an air source tubing;

b) a generally hollow valve head attached to the handle, the valve head including a water valve and an air valve;

c) a manifold assembly positioned inside the valve head, the manifold assembly including a spindle for receiving a syringe tip to be mounted thereon;

d) the manifold assembly further including a water vein for transporting water from the water source through the spindle and into a water passageway in the syringe tip;

e) the manifold assembly further including an air vein for transporting air from the air source into an air passageway in the syringe tip;

f) a thumb nut and locking collar attached to the valve head for securing the syringe tip on the spindle and adjacent a first end of the manifold body; and g) the manifold assembly further including at least one fiberoptic bundle aperture for receiving the fiberoptic bundle from the handle and positioning one end of the fiberoptic bundle adjacent the first end of the manifold body whereby when the fiberoptic bundle is illuminated, light will be directed from the fiberoptic bundle into a proximate end of a syringe tip to be mounted on the spindle so that light may be transmitted along the length of the syringe tip and emit from a remote end thereof whereby a dentist may illuminate a work area using the light emitting from the syringe tip.

4. The assembly of claim 3 further including a light transmitting syringe tip mounted on the spindle.

* * * * *